United States Patent
Durdagi et al.

(10) Patent No.: US 12,398,128 B2
(45) Date of Patent: Aug. 26, 2025

(54) PHYSICS-DRIVEN DISCOVERY OF NOVEL SMALL THERAPEUTIC COMPOUNDS FOR USE AS A BCL-2 INHIBITOR

(71) Applicant: BAHCESEHIR UNIVERSITESI, Besiktas/Istanbul (TR)

(72) Inventors: Serdar Durdagi, Besiktas/Istanbul (TR); Timucin Avsar, Besiktas/Istanbul (TR); Muge Didem Orhan, Besiktas/Istanbul (TR); Gurbet Cacan, Besiktas/Istanbul (TR); Berna Dogan, Besiktas/Istanbul (TR); Seyma Calis, Besiktas/Istanbul (TR)

(73) Assignee: BAHCESEHIR UNIVERSITESI, Istanbul (TR)

( * ) Notice: Subject to any disclaimer, the term of this patent is extended or adjusted under 35 U.S.C. 154(b) by 400 days.

(21) Appl. No.: 17/929,007

(22) PCT Filed: Feb. 10, 2021

(86) PCT No.: PCT/TR2021/050120
§ 371 (c)(1),
(2) Date: Aug. 10, 2022

(87) PCT Pub. No.: WO2021/162666
PCT Pub. Date: Aug. 19, 2021

(65) Prior Publication Data
US 2023/0109522 A1   Apr. 6, 2023

(51) Int. Cl.
*C07D 417/04* (2006.01)
*A61K 45/06* (2006.01)
*A61P 35/00* (2006.01)

(52) U.S. Cl.
CPC ............ *C07D 417/04* (2013.01); *A61K 45/06* (2013.01); *A61P 35/00* (2018.01)

(58) Field of Classification Search
None
See application file for complete search history.

(56) References Cited

U.S. PATENT DOCUMENTS

2009/0163545 A1   6/2009   Goldfarb

OTHER PUBLICATIONS

Georg E. Winter et al., Phthalimide conjugation as a strategy for in vivo target protein degradation. Science 348, 1376-1381 (2015) (Year: 2015).*

(Continued)

*Primary Examiner* — Jeffrey S Lundgren
*Assistant Examiner* — Anthony Joseph Seitz
(74) *Attorney, Agent, or Firm* — RAPHAEL BELLUM PLLC

(57) ABSTRACT

The invention relates to compound shown with formula (I) or a pharmaceutically acceptable derivative thereof for use as a novel inhibitor of BCL-2.

(I)

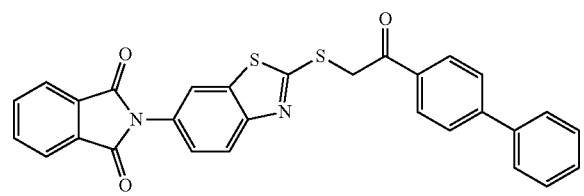

6 Claims, 1 Drawing Sheet

(56) References Cited

OTHER PUBLICATIONS

Deeks, E.D. Venetoclax: First Global Approval. Drugs 76, 979-987 (2016) (Year: 2016).*
Philoppes. J. N ., & Lamie. P. F. (2019). Design and synthesis of new benzoxazole/ benzothiazole-phthalimide hybrids as antitumor-apoptotic agents. Bioorganic chemistry, 89, 102978.
Pizzirani. D ., Roberti. M ., Grimaudo. S ., Di Cristina. A ., Pipitone. R. M ., Tolomeo. M ., & Recanatini. M. (2009). Identification of biphenyl-based hybrid molecules able to decrease the intracellular level of Bcl-2 protein in Bcl-2 overexpressing leukemia cells. Journal of medicinal chemistry. 52(21). 69 36-69 40.
Norman. D. D ., Ibezim. A ., Scott. W. E ., White. S ., Parrill. A. L., & Baker. D. L. (2013). Autotaxin inhibition: development and application of computational tools to identify site-selective lead compounds. Bioorganic & medicinal chemistry. 21(17). 5548-5560.
Wen. M ., Deng. Z. K., Jiang. S. L., Guan. Y. D ., Wu. H. Z ., Wang. X. L., . . . & Cheng. Y. (2019). Identification of novel Bcl-2 inhibitor by ligand-based screening and investigation of its anti-Cancer effect on human breast Cancer cells. Frontiers in pharmacology. 10. 391.
Tutumlu. G ., Dogan. B ., Avsar. T ., Orhan. M. D ., Calis. S ., & Durdagi. S. (2020). Integrating ligand and target-driven based virtual screening approaches with in vitro human cell line models and time-resolved fluorescence resonance energy transfer assay to identify novel hit compounds against BCL-2. Frontiers in chemistry. 8. 167.
International Search Report in International Application No. PCT/TR2021/050120 dated May 24, 2021.

* cited by examiner

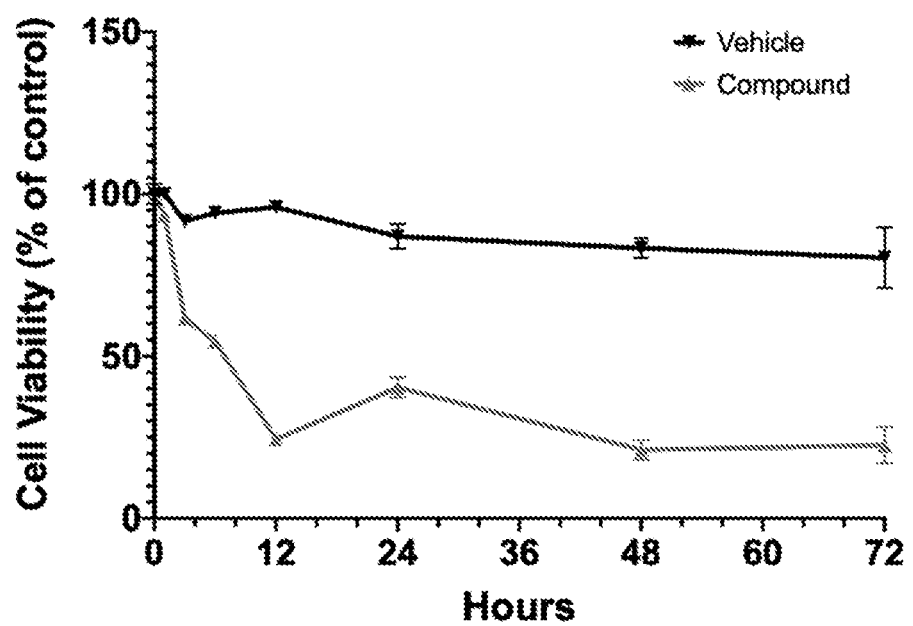

PHYSICS-DRIVEN DISCOVERY OF NOVEL SMALL THERAPEUTIC COMPOUNDS FOR USE AS A BCL-2 INHIBITOR

TECHNICAL BACKGROUND

Finding a cure for cancer is still a demanding mission in spite of the fact that molecular mechanisms and causal relationships participating in the, pathology of cancer have been comprehended since the mid-1980s. Programmed cell death, also known as apoptosis, is a molecular pathway that results with self-destruction of the cell either following termination of physiological function, or after a crucial damage to genetic material. The well-defined basic apoptosis pathways, extrinsic and the intrinsic pathways are variously stimulated, and they use determined signaling elements. The extrinsic pathway is activated by outer stimulation of death receptors. Death receptors are members of the tumor necrosis factor (TNF) receptor family which has an intracellular death domain that is able to accumulate and trigger caspase-8 followed by operation of effector caspases including caspase-3, -6 or -7. This accumulation is not accompanied by direct participation of B-cell leukemia/lymphoma-2 (BCL-2). The intrinsic pathway also called mitochondrial pathway is initiated by a variety of cytotoxic damages or growth signals, some of which are genetic instability, inadequate developmental stimulation, invasion by viral pathogens. BCL-2 tightly regulates this process and subsequently leads to the activation of caspase-9 (Cory et al., 2003; Eimon et al., 2010; Youle et al., 2008).

All members of BCL-2 protein family have retained sequence patterns regarded as the BCL-2 homology (BH) domains and could be divided into 3 main classes. The first class of proteins are made up of the pro-apoptotic activator BH domain 3 (BH3) only proteins such as BIM, BID, PUMA. Immediately upon their activation, they serve as molecular guardians that connect outer spurs to the mitochondrial pathway. The following group contains the proapoptotic effectors which are multidomain proteins, such as BAX, BAK and each of them has three BH domains. These proteins distort the integrity of mitochondrial outer membrane, which leads to free movement of cytochrome C to cytoplasm, initiates downstream caspase activity, and ultimately to the termination of cell, as soon as triggered. The last class of BCL-2 family are the antiapoptotic protein, BCL-XL, BCL-2, MCL-1, etc. All of these members consist of four BH domains and keeps cells safe by segregating their proapoptotic peers. The most important point in promoting apoptosis is to increase the amount of BH3-only proteins or switch off one of its antiapoptotic BCL-2 counterparts.

Apoptotic cell death is an innate hurdle to growth of tumor cells, hence one of the key hallmarks of cancer cells is the avoidance of apoptosis which comprises a crucial process in resistance to chemotherapeutics. This phenomenon led peculiar approaches in anticancer therapies focusing on apoptosis including suppression of survival factors that are detected to be overexpressed in numerous malignancies.

STATE OF THE ART

The idea of BH3 mimetics as promising anticancer drugs inspired by the conclusion that a great deal of cancers rely on BCL-2 family proteins and that the interaction between these proteins occur through specific BH domains. A genuine BH3 mimetic is expected to imitate the BH3 domain of a proapoptotic BCL-2 protein, thus deactivating the antiapoptotic family members by filling up their BH3-binding pockets.

Inhibition of anti-apoptotic protein BCL-2 that is overexpressed in cancer cells is one of the most studied approaches in cancer research. Currently, venetoclax is the only approved drug by Food and Drug Administration (FDA) for the treatment chronic lymphocytic leukemia (CLL) and it is a selective BCL-2 protein inhibitor. Although it has a very high affinity for BCL-2 as shown in various studies performed on different cancer cell lines, resistance to this drug have already been observed. Hence, it is necessary to suggest new compounds and scaffolds as BCL-2 inhibitors that could be more efficient against mutations on the target structure and have no side effects.

The inventors have found that a new compound shown with Formula I acts as an inhibitor of BCL-2.

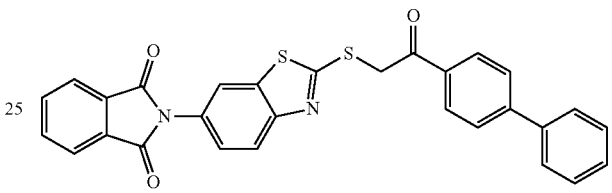

Formula I

The compound shown with formula I according to present invention is thus a representative of a novel compound that is suitable for use in several disorders where an inhibition of BCL-2 protein produces a therapeutically desirable result. Such diseases can for example be proliferative diseases such as cancer. Therefore, present invention not only relates to novel compounds shown with formula I but also to use of said compounds for treatment of proliferative diseases such as cancer.

BRIEF DESCRIPTION OF THE DRAWING

FIG. 1 depicts the cell viability over time, as determined by MTT assay, of vehicle-treated HCT-116 cells and HCT-116 cells treated with the compound of formula I.

DETAILED DESCRIPTION OF THE INVENTION

The invention relates to compound shown with formula I, which is DRG-BCL2-3, or a pharmaceutically acceptable derivative thereof.

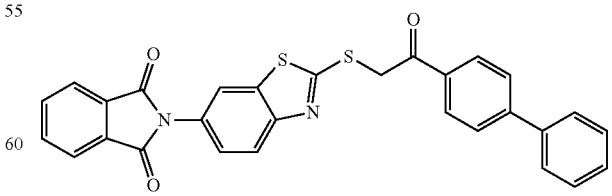

Formula I

Unless specified otherwise, the terms "compound of the present invention" or "compound of invention" or "compound of formula I" or "compound shown with formula I" are used interchangeable and refer to compounds of formula I and salts thereof, hydrates or solvates of the compound of formula I or its salts, all possible stereoisomers (diastereomers and enantiomers), tautomers, isotopically labeled compounds (including deuterium substitutions), or its forms that form under physiological conditions of the human body, as well as inherently formed moieties (e.g., polymorphs, solvates and/or hydrates).

In other words, the term "pharmaceutically acceptable derivative thereof" refers to hydrates, solvates, prodrugs, all possible stereoisomers, salts, esters, tautomers, isotopically labeled derivatives or forms of compound of formula I that form under physiological conditions of the human body.

Several embodiments of the invention are described herein. It must be considered that each specified embodiment can be combined with other specified features to provide further embodiments. The terms used in the singular will also include plural and vice versa.

As disclosed herein the term "enantiomers" mean a pair of stereoisomers that are non-superimposable mirror images of each other. A 1:1 mixture of a pair of enantiomers is a "racemic" mixture. The absolute stereochemistry is specified according to the Cahn-Ingold-Prelog R-S system. When a compound is a pure enantiomer the stereochemistry at each chiral carbon may be specified by either R or S. Compound of formula I has a chiral center. In a preferred embodiment of the invention compound of formula I is in the form of a 1:1 racemic mixture of R and S enantiomers. The compound of formula I can also be in pure R form or in pure S form or a mixture thereof in any ratio.

The present invention includes all possible isomers including racemates and optically pure forms of compound of formula I. Said forms can be prepared by using conventional techniques known in the art such as by use of chiral reagents or other methods.

As disclosed herein the term "salts" mean acid addition of base addition salts of the compound of invention. In particular the salts include "the pharmaceutically acceptable salts" which refer to salts that retain the biological effectiveness and effectiveness of the compound of invention while not having any biologically or otherwise unwanted properties such as toxicity or causing any kind of formulation difficulties.

Pharmaceutically acceptable acid addition salts can be formed with organic acids and/or inorganic acids. Acid addition salts of the compound according to present invention can be selected from a group comprising; acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, lauryl sulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Pharmaceutically acceptable base addition salts can be formed with organic bases and/or inorganic bases. Bases appropriate for preparation of base addition salts of the compound of the invention can be selected from sodium hydroxide, sodium carbonate, sodium bicarbonate, calcium hydroxide, calcium carbonate, calcium bicarbonate, magnesium hydroxide, magnesium carbonate, magnesium bicarbonate, potassium hydroxide, potassium carbonate, potassium bicarbonate and the like.

As disclosed herein the term "isotopically labeled compounds" refers to compounds of formula I wherein one or more atoms are replaced with an atom having selected atomic mass or mass number. Such replacements can be made with for example; $^{2}$H, $^{3}$H, $^{11}$C, $^{13}$C, $^{14}$C, $^{15}$N, $^{18}$F, $^{31}$P, $^{32}$P, $^{35}$S, $^{36}$Cl, $^{125}$I. Such isotopically labeled variants of compound of the invention can be used for detection or imaging techniques known in the art or for radioactive treatment of patients.

In another aspect present invention relates to pharmaceutical compositions comprising compound of formula I, DRG-BCL2-3, or a pharmaceutically acceptable derivative thereof and at least one pharmaceutically acceptable excipient.

In a preferred embodiment of the invention, the pharmaceutically acceptable excipient can be selected from a group comprising; solvents, antioxidants, preservatives (e.g. antibacterial agents, antifungal agents), isotonic agents, absorption delaying agents, salts, preservatives, stabilizers, binders, disintegrants, lubricants, sweetening agents, flavoring agents and combinations thereof. Particular examples of each group are disclosed in Remington's Pharmaceutical Sciences, 18th Ed. Mack Printing Company, 1990 and incorporated herein by reference.

The pharmaceutical compositions comprising compound of formula I or a pharmaceutically acceptable derivative thereof can be formulated for different routes of administration. In an embodiment of the invention, pharmaceutical compositions comprising compound of formula I can be formulated for oral administration, parenteral administration, topical administration or rectal administration.

In a preferred embodiment of the invention, pharmaceutical compositions of the invention for oral administration can be in the form of tablets, lozenges, aqueous or oily suspensions, dispersible powders or granules, emulsion, hard or soft capsules, or syrups or elixirs.

In a preferred embodiment of the invention, pharmaceutical compositions of the invention for parenteral administration can be in the form of isotonic solutions or suspensions or in to form of lyophilized powder suitable for reconstitution prior to administration. Said pharmaceutical compositions of the invention for parenteral administration can be for intramuscular, intravenous, subcutaneous, intraperitoneal, intratracheal administration.

In a preferred embodiment of the invention, pharmaceutical compositions of the invention for topical administration can be in the form of aqueous solutions, suspensions, ointments, pastes, lotions, transdermal patches, gels, creams, or sprayable formulations such as aerosols. Such topical administration covers administration through skin, eye or nose (i.e. intranasal administration). Thus, pharmaceutical compositions of the invention can be in the form of dry powders, solutions or aerosols for administration through pressurized containers, pump, spray, atomizer or nebulizer with or without a suitable propellant.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

In a preferred embodiment, the invention, relates to compound of formula I, DRG-BCL2-3, or a pharmaceutically acceptable derivative thereof for use in treatment of a disorder mediated by the activity (including normal activity or especially over activity) of BCL2.

In an embodiment, the invention relates to compound of formula or a pharmaceutically acceptable derivative thereof for use in treatment of a disorder wherein a desirable therapeutic response is observed upon administration of a BH3 mimetic.

Within the context of this application the terms "BCL-2 inhibitor" and "BH3 mimetic" refer to the same compounds and can be used interchangeably.

In a preferred embodiment, a disorder mediated by the activity of BCL2 is a proliferative disease such as cancer.

In an embodiment of the invention, cancer includes benign or malignant tumors, a soft tissue sarcoma or a sarcoma (e.g. liposarcoma, rhabdomyosarcoma) or bone cancer (e.g. osteosarcomas), a carcinoma (e.g. such as of the brain, kidney, liver, adrenal gland, bladder, breast, gastric, ovary, colon, rectum, prostate, pancreas, lung, vagina or thyroid), a glioblastoma, meningioma, glioma, mesothelioma, a multiple myeloma, a gastrointestinal cancer (especially colon carcinoma or colorectal adenoma), a tumor of the head and neck, a melanoma, a prostate hyperplasia, a neoplasia, a neoplasia of epithelial character, a leukemia such as acute myeloid leukemia or B-cell chronic lymphocytic leukemia, a lymphoma (such as of B- or T-cell origin) and metastases in other organs.

In another aspect the invention relates to the use of a compound of formula I or a pharmaceutically acceptable derivative thereof as defined herein, for the manufacture of a medicament for the treatment of a disorder or a disease in a subject mediated by the activity of BCL2.

In another aspect, the invention relates to combinations comprising compound of formula I or pharmaceutically acceptable derivatives thereof and one or more additional active agent selected from a group comprising; anti-proliferative agents, immunomodulatory agents, antiviral agents, antimicrobial agents, anti-infective agents, anti-inflammatory agents, anesthetic agents, antiemetics or combinations thereof where appropriate. In a preferred embodiment additional active agent is one or more anti-proliferative agent.

In an embodiment of the invention, anti-proliferative active agent can be one or more of the agents selected from the group comprising but not limited to; alkylating agents, anthracyclines, taxanes (cytoskeletal disruptors), epothilones, histone deacetylase inhibitors, inhibitors of topoisomerase I, inhibitors of topoisomerase II, kinase inhibitors, tyrosine kinase inhibitors, nucleotide analogs and precursor analogs, peptide antibiotics, platinum based agents, retinoids, vinca alkaloids and derivatives or other agents.

Alkylating agents can be selected from a group comprising but not limited to; bendamustine, cyclophosphamide, mechlorethamine, chlorambucil, melphalan, dacarbazine, nitrosoureas, streptozotocin, temozolomide, trabectedin.

Anthracyclines can be selected from a group comprising but not limited to; daunorubicin, doxorubicin, epirubicin, idarubicin, mitoxantrone, valrubicin.

Taxanes (cytoskeletal disruptors) can be selected from a group comprising but not limited to; paclitaxel, docetaxel, abraxane, cabazitaxel, Epothilones can be selected from a group comprising but not limited to; epothilone A, epothilone B, epothilone C, epothilone D, epothilone E, epothilone F or pharmaceutically acceptable derivatives thereof such as ixabepilone.

Histone deacetylase inhibitors can be selected from a group comprising but not limited to; belinostat, panobinostat, valproate, vorinostat, romidepsin.

Inhibitors of topoisomerase I can be selected from a group comprising but not limited to; irinotecan, topotecan.

Inhibitors of topoisomerase II can be selected from a group comprising but not limited to; etoposide, teniposide, tafluposide.

Kinase inhibitors can be selected from a group comprising but not limited to; bortezomib, erlotinib, gefitinib, imatinib, vemurafenib, vismodegib.

Tyrosine kinase inhibitors can be selected from a group comprising, but not limited to, afatinib, axitinib, bosutinib, cobimetinib, crizotinib, dasatinib, erlotinib, gefitinib, imatinib, lapatinib, nilotinib, osimertinib, pazopanib, ruxolitinib, sunitinib, vandetanib.

Nucleotide analogs and precursor analogs can be selected from a group comprising but not limited to; azacitidine, azathioprine, cladribine, clofarabine, capecitabine, cytarabine, doxifluridine, decitabine, floxuridine, fludarabine, fluorouracil (5-FU), fluorouracil, gemcitabine, hydroxyurea, mercaptopurine, methotrexate, nelarabine, pentostatin, tioguanine, trifluridine, tipiracil.

Peptide antibiotics can be selected from a group comprising but not limited to; bleomycin, actinomycin.

Platinum based agents can be selected from a group comprising but not limited to; carboplatin, cisplatin, oxaliplatin.

Retinoids can be selected from a group comprising but not limited to; tretinoin, alitretinoin, bexarotene, isotretinoin, tamibarotene.

Vinca alkaloids and derivatives can be selected from a group comprising but not limited to; vinblastine, vincristine, vindesine, vinflunine, vinorelbine.

Other agents can be selected from a group comprising but not limited to; methotrexate, pemetrexed, pralatrexate, raltitrexed, etoposide teniposide, abiraterone, bicalutamide, cyproterone, degarelix, exemestane, fulvestrant, goserelin, histrelin, leuprolide, mifepristone, triptorelin, lenalidomide, pomalidomide, thalidomide, everolimus, temsirolimus, anagrelide, ceritinib, dabrafenib, idelalisib, ibrutinib, palbociclib, vemurafenib, bleomycin, dactinomycin, eribulin, estramustine, ixabepilone, mitomycin, procarbazine, alectinib, fluoxymesterone, iobenguane, imiquimod, interferon, ixazomib, lanreotide, lentinan, octreotide, omacetaxine, tegafur, gimeracil, oteracil, uracil, combretastatin.

In an embodiment of the invention, such combinations can be in a form wherein compound of formula I or a pharmaceutically acceptable derivative thereof and one or more therapeutically active agents, preferably anti-proliferative agents are formulated together.

In another embodiment of the invention, compound of formula I or a pharmaceutically acceptable derivative thereof and one or more therapeutically active agents, preferably anti-proliferative agents are formulated separately but they are administered to a patient in need thereof simultaneously or sequentially.

Comprising in the context of the present specification is intended to meaning including.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

The invention will now be described with reference to the following examples, which are merely illustrative and should not in any way be construed as limiting the scope of the present invention.

EXAMPLES

Example 1: Cell Culture Experiments

For cell culture experiments various cancer cell lines, HCT-116 colon cancer, U87-MG glial tumor, MCF7 breast cancer cell lines were used. Cells were seeded with high glucose DMEM medium (Biosera) supplemented with 10% FBS (Gibco) and 1× penicillin/streptomycin (Multicell). Twenty-four hours prior to molecule treatment, 10,000 cells were seeded into each well of 24-well cell culture plates. Molecules were used by preparing 4 mM stock solution in DMSO (Amresco). For molecule treatment, molecule stock solutions were diluted in DMEM with 10% FBS and added onto cells in each corresponding well. Final concentration of vehicle DMSO was 2% at maximum. Therefore, the vehicle group in experiments only included maximum of 2% DMSO concentration. We calculated the number of cells to be seeded to make sure that none of the cells reaches more than 60% confluency during the treatment period, as higher plate confluency levels would slow down cell proliferation independently from the molecule treatment.

Values of half-maximal inhibitory concentration were (IC50) determined by MTT cell proliferation assays. Different concentrations of molecules ranging between 10-9 to 10-4 M were tested on HCT-116 cell lines with single treatment. 570 nm absorbance values were recorded and IC50 values were calculated by dose response-inhibition curves and nonlinear regression analysis on GraphPad Prism 8 software. For cell proliferation assays we performed five days experiments and repeated experiments at least three times with all cell lines. Survival rates did not change significantly after third day of treatment. Therefore, three days results were presented. MTT analysis were performed on 24-well plates with initially 1×104 cells/well, grown overnight, and then treated with the selected molecules with different concentrations for at least 3 days. Following the initial incubation day, molecules were added and after incubation with MTT at 37° C. for 4 hours, formazan was solubilized with DMSO (Sigma-Aldrich, St. Louis, USA) and absorbance was measured at 570 nm. As shown by the graph in FIG. 1, while the vehicle group show neat proliferation of the HCT-116 cells, the group treated with compound of formula I has shown reduced proliferation and apoptotic cell structures. The IC50 value of compound of formula I was determined to be 22 μm (FIG. 1).

The invention claimed is:

1. A compound shown with formula I which is DRG-BCL2-3, or a pharmaceutically acceptable derivative thereof,

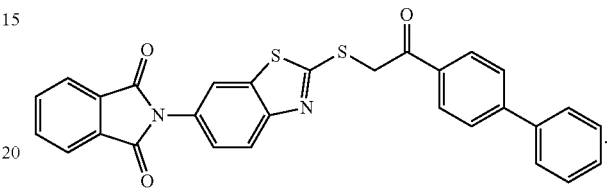

Formula I

2. The compound according to claim 1, wherein the pharmaceutically acceptable derivative of formula I is a hydrate, a solvate, a stereoisomer, a salt, an ester, a tautomer, or an isotopically labeled derivative thereof.

3. A pharmaceutical composition comprising a compound according to claim 1 and at least one pharmaceutically acceptable excipient.

4. A pharmaceutical composition comprising a compound according to claim 1 and one or more additional pharmaceutically active agent selected from the group consisting of anti-proliferative agents, immunomodulatory agents, antiviral agents, antimicrobial agents, anti-infective agents, anesthetic agents, antiemetics, and combinations thereof.

5. The pharmaceutical composition of claim 4, wherein the antiproliferative agents are selected from the group consisting of alkylating agents, anthracyclines, taxanes or cytoskeletal disruptors, epothilones, histone deacetylase inhibitors, inhibitors of topoisomerase I, inhibitors of topoisomerase II, kinase inhibitors, tyrosine kinase inhibitors, nucleotide analogs and precursor analogs, peptide antibiotics, platinum-based agents, retinoids, *vinca* alkaloids, and derivatives thereof.

6. The pharmaceutical composition of claim 4, wherein the antiproliferative agents are selected from the group consisting of methotrexate, pemetrexed, pralatrexate, raltitrexed, etoposide teniposide, abiraterone, bicalutamide, cyproterone, degarelix, exemestane, fiilvestrant, goserelin, histrelin, leuprolide, mifepristone, triptorelin, lenalidomide, pomalidomide, thalidomide, everolimus, temsirolimus, anagrelide, ceritinib, dabrafenib, idelalisib, ibrutinib, palbociclib, vemurafenib, bleomycin, dactinomycin, eribulin, estramustine, ixabepilone, mitomycin, procarbazine, alectinib, fluoxymesterone, iobenguane, imiquimod, interferon, ixazomib, lanreotide, lentinan, octreotide, omacetaxine, tegafur, gimeracil, oteracil, uracil, and combretastatin.

* * * * *